United States Patent [19]

Webber et al.

[11] 4,247,780
[45] Jan. 27, 1981

[54] FEEDBACK CONTROLLED GEOMETRY REGISTRATION SYSTEM FOR RADIOGRAPHS

[75] Inventors: Richard L. Webber, Rockville; Roger N. Nagel, Silver Spring, both of Md.

[73] Assignee: The United States of America as represented by the Department of Health, Education and Welfare, Washington, D.C.

[21] Appl. No.: 46,826

[22] Filed: Jun. 8, 1979

[51] Int. Cl.³ ............................ A61B 6/00; A61B 6/08
[52] U.S. Cl. ............................. 250/491; 250/416 TV; 250/445 T
[58] Field of Search ............. 250/445 T, 416 TV, 491

[56] References Cited

U.S. PATENT DOCUMENTS

| 4,010,370 | 3/1977 | LeMay | 250/445 T |
| 4,045,672 | 8/1977 | Watanabe | 250/445 T |
| 4,051,378 | 9/1977 | Krippner | 250/445 T |
| 4,057,725 | 11/1977 | Wagner | 250/445 T |
| 4,118,631 | 10/1978 | Froggatt | 250/445 T |
| 4,135,095 | 1/1979 | Watanabe | 250/445 T |

*Primary Examiner*—Alfred E. Smith
*Assistant Examiner*—T. N. Grigsby

*Attorney, Agent, or Firm*—Browdy and Neimark

[57] ABSTRACT

A system for reproducibly aiming an X-ray source array to provide substantial registration of exposure geometry through an organ or a portion of tissue from one examination to the next. The system derives functions or signals based on computer controlled X-ray source point geometries to create multiple images produced from known positions via a detector array which feeds this information to a computer image storage system and which provides for comparison of the detected signals with reference signals originally stored in a memory; the comparison yields correction signals which act to shift the X-ray raster toward restoration of the original effective geometry. Thus, the X-ray sources are coupled to the detector array through a feedback loop circuit including a computer which, by sequentially activating each X-ray point source and noting the resulting functions generated by the detector array, can compare the results with the stored functions and revise the working geometry to simulate that of the original geometry from which the stored reference functions were obtained. The computer also activates a visual display device providing a crude X-ray scan through the tissue of interest, which can be used to create low resolution tomograms of the irradiated structures.

10 Claims, 3 Drawing Figures

FEEDBACK CONTROLLED GEOMETRY REGISTRATION SYSTEM FOR RADIOGRAPHS

FIELD OF THE INVENTION

This invention relates to radiography systems, and more particularly to methods and apparatus for reproducibly aiming X-ray sources in order to achieve registration of exposure geometry from one examination to the next.

BACKGROUND OF THE INVENTION

Various devices have been proposed for obtaining desired radiographic alignments of X-ray sources relative to viewing screens or films. These have included electro-optical devices and various mechanical devices, to stabilize the geometry. However, none are automated via a feedback loop, or equivalent means, so as to determine appropriate geometry during the radiographic process. Therefore, there is a need to overcome this shortcoming, for example by the use of a multiple-source system which provides two-dimensional registration based on user selectable criteria and which can involve all aspects of the radiographic image, including data derived from previous examinations.

A preliminary search of the prior art reveals the following prior U.S. patents of interest, which appear to show the present state of the patented art:

Hartmann, U.S. Pat. No. 3,673,394
Gasaway, U.S. Pat. No. 3,714,428
Damman et al, U.S. Pat. No. 3,873,834
Ennslin et al, U.S. Pat. No. 3,906,227
Cowell et al, U.S. Pat. No. 3,932,756
Albert, U.S. Pat. No. 3,949,229
Zermano et al, U.S. Pat.-No. 4,085,324

Also of interest, and pertinent to the subject matter of the present invention, are the following publications:

Fujimura et al, "Computer Controlled Radiography for Observation of Movements of Articulatory and Other Human Organs", Comput. Biol. Med., Pergamon Press (Great Britain), 1973, Vol. 3, pp. 371-384.

McKee et al, "Computer Recognition of Partial Views of Curved Objects", IEEE Transactions on Computers, Vol. C-26, No. 8, August 1977, pp 790-800.

Wong, "Sensor Transformations", IEEE Transactions on Systems, Man and Cybernetics, Vol. SMC-7, No. 12, December 1977, pp 836-841.

Ulstad, "An Algorithm for Estimating Small Scale Differences Between Two Digital Images", Pattern Recognition, Pergamon Press (Great Britain), 1973, Vol. 5, pp 323-333.

Perry et al, "Medical Image Reconstruction: Multiangular Sectional Roentgenography by Computer", NCAR Technical Note (National Center for Atmospheric Research, Boulder, Colo.), August 1975, NCAR-TN/STR-108.

SUMMARY OF THE INVENTION*

*Please see Proceedings of May 16, 1978 "Workshop on Feedback Control of Exposure Geometry in Dental Radiation", incorporated by reference herein.

The system of the present invention is based on the coupling of an array of X-ray sources to a suitable X-Y addressable detector array via a computer in a feedback-loop circuit. The tissue sample of interest is placed between a loosely collimated variable site of an activation source array and a high-resolution detector array. The source array defines selectively positioned X-ray point sources which can be shifted in space relative to the tissue sample of interest. The detector array has spatial and temporal resolution consistent with the radiation from said point sources. By sequentially activating each loosely collimated source point and noting (and storing) the characteristics of the resulting images, the computer can in a subsequent examination compare results and select for the source geometry which optimizes performance for the diagnostic task.

Within the general concept of the present invention, if it is more practical or easier to activate all source points simultaneously, a suitable computer may be employed to deconvolute the multiple images to yield a similar result, provided that the contribution from each source point can be unequivocally identified.

The dosage can be minimized by limiting exposure during the "search" process to an amount only sufficient to permit reliable identification of changes in exposure geometry brought about by activation of the different source points.

Since the ultimate image is expressed as a time varying signal which is fed to the computer, the effective dynamic range (which determines the signal-to-noise ratio) is limited only by the storage capacity of the computer. Sophisticated image processing algorithms would permit nearly all of the information acquired during the search to be used to refine the ultimate image. Conversely, the quality of the image (and hence the required dose to the patient) can be tailored to any particular diagnostic task.

To the extent that the multiple-point sources can be sequentially activated to produce a crude scan, the device can also be used to create low-resolution tomograms of any of the irradiated structures.

Accordingly, a main object of the invention is to provide a novel and improved feedback-controlled geometry registration system for radiographs which overcomes the deficiencies and disadvantages of prior systems employed for registration of exposure geometry from one examination to the next.

A further object of the invention is to provide an improved automated system of radiography which stabilizes exposure geometry via a feedback loop which takes into account the geometry associated with prior examinations and which minimizes exposure during the geometry-stabilization process.

A still further object of the invention is to provide an improved automated radiography geometry-stabilizing system which employs sequential activation of loosely collimated point-radiation sources for traversing a tissue portion of interest and for generating geometry-characterizing signals which are stored in a computer and which are subsequently employed as geometry-comparison signals representing the initial effective geometry in subsequent irradiations of said tissue portion by the same array and sequence of point sources, so as to enable effective approximation of the original geometry and thereby optimize diagnostic performance.

A still further object of the invention is to provide an improved automated system of radiography which controls exposure geometry via a feedback loop including a computer, and which stores signals representing the geometry of a prior examination and which uses these stored signals as reference data for effectively recreating the original geometry in subsequent examinations of the same tissue portion, the system being also adaptable for producing a scan which can be used to create low resolution tomograms of the irradiated structures.

A broad object is to provide for improved radiography techniques, and a further broad object is to obtain more accurate information through radiography.

BRIEF DESCRIPTION OF THE DRAWINGS

Further objects and advantages of the invention will become apparent from the following description and claims, and from the accompanying drawings, wherein:

DESCRIPTION OF A PREFERRED EMBODIMENT

In the radiographic examination of a portion of tissue or a body structure and the monitoring of changes therein over a period of time or over a series of treatments, it is important to always use substantially the same orientation and positioning of the tissue portion or structure in the radiographic field, particularly where internal structural details must be monitored.

It is highly desirable to be able to reproduce the location of the tissue portion or structure under study relative to the X-ray beam from one examination to the next. For this purpose it is necessary to be able to establish a basis for determining the position of tissues relative to the source-detector mechanism. No satisfactory general method or means of achieving this purpose has been heretofore available.

The present invention relies on the use of an effective source array made possible by moving the focal spot of the X-ray beam on an enlarged target. However, any mechanism for generating X-rays from various computer-adjustable points in the source plane is acceptable. The changes in exposure geometry made possible by this source array are used to establish reference data for positive registration or for correction of improper registration from one X-ray examination to the next.

Figure 1:
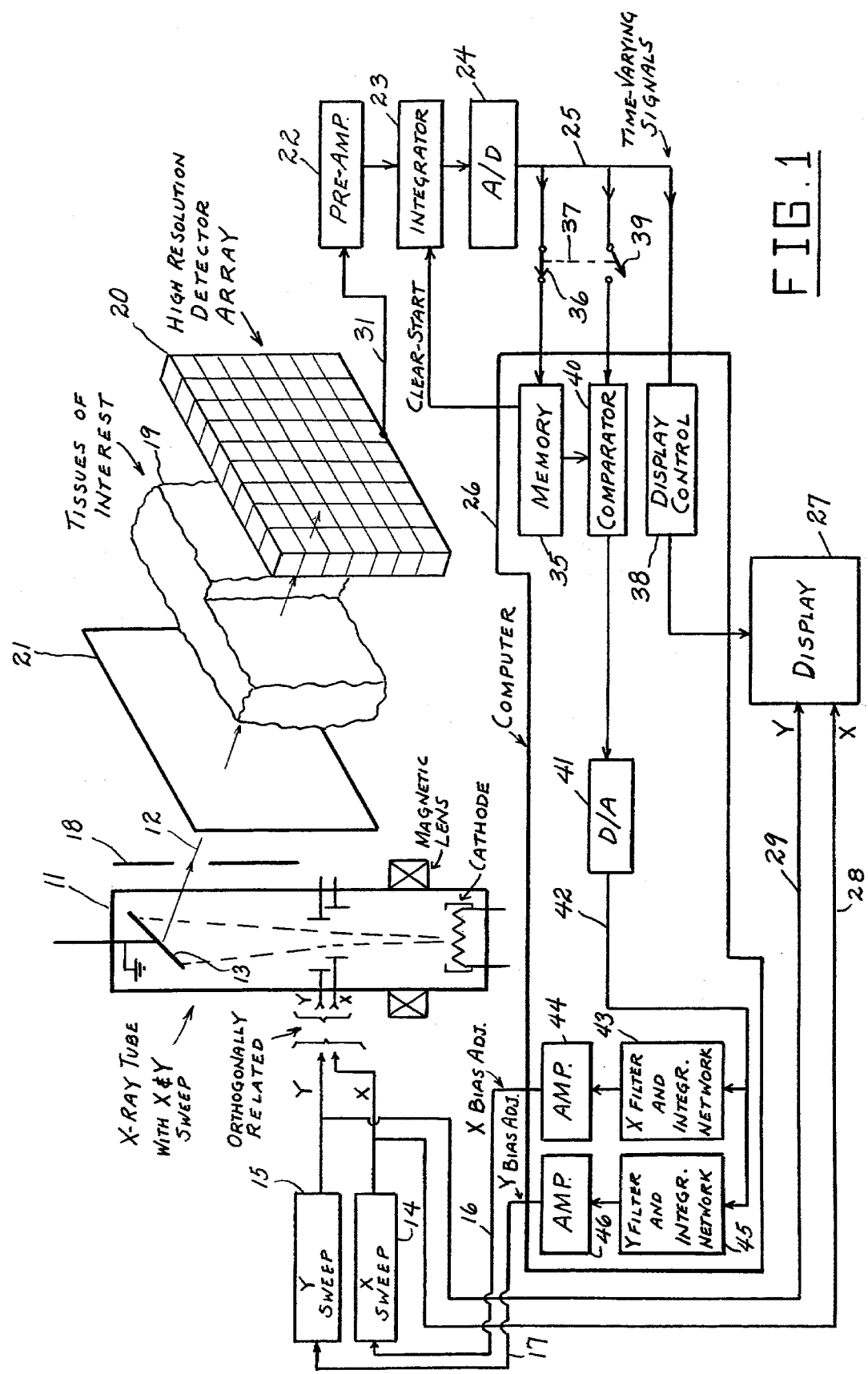
FIG. 1 is a schematic block diagram of a typical feedback-controlled radiography system constructed in accordance with the present invention.

Referring to the drawings, FIG. 1 diagrammatically illustrates a typical radiographic system according to the present invention, including an X-ray tube 11 of the deflection type, which may be generally similar to that described in Fujimura et al, "Computer Controlled Radiography for Observation of Movements of Articulatory and Other Human Organs", Comput. Biol. Med., Pergamon Press (Great Britain) 1973, Vol. 3, pp. 371–384. In this unit the X-ray source (the electron beam spot on the target) is small in diameter and has high brightness so that a high-resolution X-ray beam 12 with substantial photon density is generated from an enlarged target 13. The electron beam is deflected in the X-Y directions by conventional X and Y sweep generators 14 and 15 with adjustable bias, supplied by bias input lines 16 and 17, so that the electron beam sweep raster on the inclined target 13 is adjustable in position in accordance with changes of the bias voltages furnished to the bias input lines 16 and 17. The positioning of the focal spot which is the source of X-rays is thus adjustable and can be determined by computer control.

The tissue or body structure of interest, shown at 19, which may be a portion of a patient's mouth, is positioned in a stationary fashion between the source 11 and a high resolution detector array 20 which may, for example, comprise an array of NaI scintillation crystals corresponding geometrically with the spatial configuration of the array of corresponding source positions, whose outputs are connected to the common output line 31 and which are sufficiently thick so that practically all of the incident photons are captured and utilized. A suitable filter 21 may be placed in front of the tissue portion 19 to eliminate softer X-rays. The radiation from the target 13 is loosely collimated by a suitably apertured gate 18 which confines the radiation so as to only intercept the detector array 20, and thereby limit the amount of radiation received by a patient under examination.

Signals corresponding to the number of photons received are generated in the detector array and are delivered via a preamplifier 22 and an integrator 23 to an analog-to-digital converter 24, appearing at the output line 25 thereof as digital signals. These signals are furnished, in a manner presently to be described, to a computer 26, which in turn furnishes X-Y deflection bias control signals to the lines 16, 17, and which supplies display signals to a display device 27, such as an oscilloscope, whose X-Y sweep is provided from the outputs of X and Y sweep generators 14 and 15 via lines 28, 29.

The location matrix of the point sources (source array) is uniformly spaced in horizontal rows and vertical columns so that the position of the source can be moved by changing the position of the electron beam on the target 13. The tissue-modulated output from each source position produces a characteristic signal in the detector array output line 31 as a function of position on the array.

Figure 2:
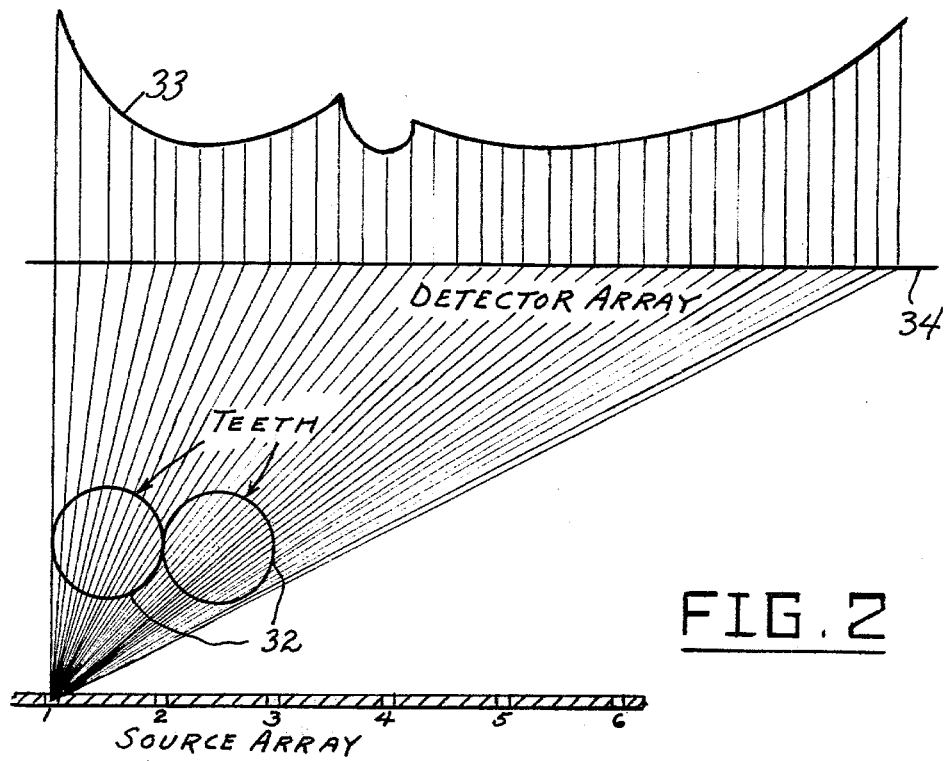
FIG. 2 is a diagram showing a dental application of the system of FIG. 1 and illustrating the radiographic output signal generated by the radiation point source at one projection point of the source array, and showing how the signal is shaped by the presence of teeth in the path of the X-ray beam from said projection point.
Figure 3:
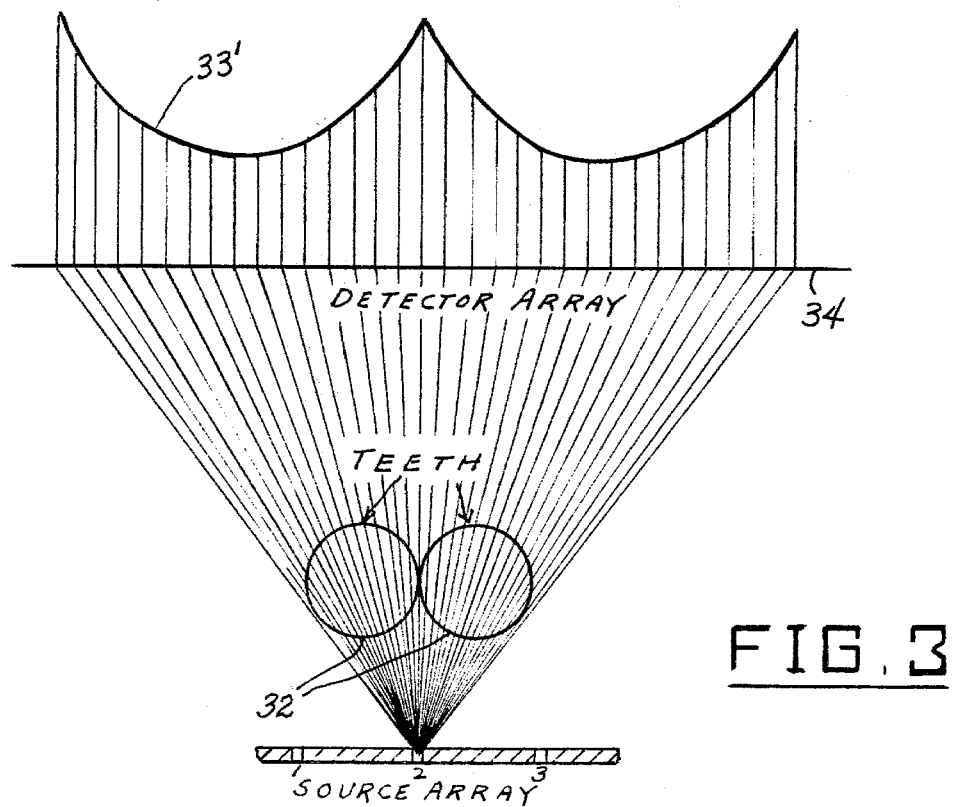
FIG. 3 is another diagram similar to FIG. 2, but showing the radiographic output signal generated by the sequential beam from an adjacent projection point in the source array.

This principle as applied to a dental examination is illustrated schematically in FIGS. 2 and 3. In this case the tissues of interest are circles 32 simulating teeth as viewed from the occlusal surfaces. The effects of changing exposure geometry produced by a change of position of the focal spot on the target 13 are shown as plots of radiographic output (determined by tissue attenuation) as a function of distance along the plane of the extroral detector array. For example, in FIG. 2 the plot 33 is a function of the distance swept in the X direction along the detector array line 34 by the moving X-ray beam 12 at position No. 1 on the target (or source array). By sequencing from one position to the next, the resulting output function changes dramatically. Thus, it can be easily seen from FIG. 3 that the output function 33' has markedly changed in shape from that of the plot 33 of FIG. 2, as a result of the small change in exposure geometry of the X-ray beam. By comparing these output functions with a known optimum, or with previously recorded functions, it is possible to optimize the projection characteristics, namely, to reproduce the spatial relationships produced by a specific projection geometry from one examination to the next.

While the functions for only two position geometries are illustrated respectively in FIGS. 2 and 3, in actual usage many source point elements are used to establish geometric stability by means of the feedback principle to be presently described. In general, the process is applied in two dimensions (width and height, i.e., X and Y) although FIGS. 2 and 3 illustrate application only in the X direction.

It is to be noted that the distance between the source elements inside the mouth has no effect on image resolution since each element in the array generates the entire radiographic image. Since the system can be easily controlled by the associated computer, image quality (information capacity) can be reduced to the minimum necessary to select the appropriate projection geometry and then increased to yield an image suitable for the diagnostic task to be accomplished.

The sequential signals (33, 33', etc.) are converted into digital form, as above described, at line 25. In the first examination these digital signals are stored in a memory 35 in the computer 26, by closure of one switch section 36 of a double-throw, two-pole switch 37. These signals also may be suitably processed in a display control unit 38 in the computer and furnished to the display device 27 to provide a visual display.

In a subsequent examination, the switch 37 is operated to open section 36 and close the remaining section 39. This connects the digital signal output line 25 to one input of a comparator 40 in the computer, the other input thereof receiving the previously stored signals from the first examination provided by the memory 35. The digital difference signals from comparator 40 are converted to analog form via a digital-to-analog converter 41, the resultant analog difference signals appearing in the converter output line 42. The X bias-adjustment voltage is derived from the composite analog difference signals via an X-filter and integration network 43 and an amplifier 44 connected between line 42 and output line 16, and the Y bias-adjustment voltage is derived from a Y-filter and integration network 45 and amplifier 46 connected between line 42 and output line 17. The respective sweep bias adjustment voltages are arranged to act on the X and Y sweep generators 14 and 15 to shift the cathode beam raster on target 13 in a direction to minimize the difference signals in line 42, and thereby substantially restore the projection geometry of the first examination. This process also can be employed for additional subsequent examinations, utilizing the original recordings retained in the memory 35.

In applications exemplified by that associated with FIGS. 2 and 3, the reciprocity of the design of the apparatus assures that the system will function irrespective of the direction of the X-rays. Hence the source array and the detector array can be functionally interchanged with no theoretical consequences. In other words, the detector array may be inside the mouth and the source array may be outside the mouth, instead of the reverse arrangement above described.

Any suitable algorithm may be employed for comparing the stored and subsequent functions to derive the required corrections for restoring the desired projection characteristics. The illustrated and above-described correction arrangement is merely an example of a typical design. While a means for comparing the detected functions with previously recorded functions can take various forms, a particularly fool-proof method involves three-dimensional reconstruction similar to the technique of Perry et al, supra.

Within the spirit of the present invention it may be advantageous to activate all the source points simultaneously and to employ a suitable computer 26 designed to deconvolute the multiple images derived from the simultaneously-activated source points, to eventually yield the same result as the above-described sequential-activation system. However, this requires that the contributions from each source location be unequivocally identified in some way.

While the typical embodiment illustrated in FIG. 1 employs a source array formed on an inclined target 13 generating X-rays of the scatter type, as an alternative within the spirit of the present invention, the source array may comprise a screen generating X-ray point sources responsive to swept cathode beam transmission, as shown in U.S. Pat. No. 3,949,229 to R. D. Albert, previously cited.

While a specific embodiment of an improved feedback controlled geometry registration system for radiography has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A radiographic tissue study apparatus comprising X-ray generating means defining selectively positioned X-ray point sources which can be shifted in space relative to a tissue sample of interest, a detector array spaced from said X-ray generating means and located in the path of radiation from said point sources and having spatial and temporal resolution consistent with the radiation from said point sources, said detector array being arranged to generate multiple radiographic image signals respectively in accordance with X-ray transmission from said point sources through such tissue sample, means to store original signals so produced, means to subsequently compare said original signals with characteristic later signals formed by the detector array by irradiation through the same tissue sample by said point sources, and means to directionally shift said point sources in accordance with such comparison so as to substantially modify the effective projection geometry if there is a difference as compared with the original projection geometry.

2. The radiographic tissue study apparatus of claim 1, and wherein said X-ray generating means includes X-ray beam deflection means of the X-Y type.

3. The radiographic tissue study apparatus of claim 1, and means to provide a visual display of the signals generated by said detector array.

4. The radiographic tissue study apparatus of claim 1, and wherein said X-ray generating means includes means to provide a predetermined repetitive point source pattern of individually addressable point sources.

5. The radiographic tissue study apparatus of claim 4, and wherein said X-ray generating means is of the cathode ray type and has beam deflection means comprising opposed pairs of orthogonally related X and Y deflection elements acting on the cathode ray of the X-ray generating means.

6. A method of reproducing the original projection geometry of a radiographic tissue examination system comprising sequentially activating a plurality of spaced X-ray beam sources located at one side of a tissue portion under study in an X-Y pattern, detecting the sequentially-transmitted X-ray beams through the tissue portion, forming sequential original respective characteristic signals from the detected X-ray beams, storing said original characteristic signals, later sequentially transmitting X-ray beams from said X-ray beam sources through the same tissue portion, detecting the later transmitted beams, forming an additional set of sequential characteristic signals from the detected later-transmitted beams, comparing the additional set of characteristic signals with the stored original characteristic signals throughout the sequences thereof to develop variable X bias and variable Y bias adjustment signals, and spatially shifting the beam directions of the activated spaced X-ray beam sources in the X and Y directions in accordance with the respective variable X bias and variable Y bias adjustment signals to reduce the differences between said original characteristic signals and said additional characteristic signals and thus substantially restore the original effective projection geometry of the system.

7. The method of claim 6, and wherein said sequential characteristic signals and said additional set of characteristic signals have respective characteristic shapes in accordance with the locations of the X-ray beam sources relative to the tissue portion.

8. The method of claim 6, including moving a focal excitation spot on an enlarged X-ray target to thereby form said plurality of X-ray beam sources.

9. A method of claim 8, wherein said sequential characteristic signals and said additional set of characteristic signals are digital signals, said comparing step compares these digital signals, and including coverting the result of the comparison to analog signals and filtering and integrating the analog signals to develop the variable X bias and variable Y bias adjustment signals.

10. A method of either claim 6 or claim 8, wherein said sequential characteristic signals and said additional set of characteristic signals are digital signals, said comparing step compares these digital signals, and including coverting the result of the comparison to analog signals and filtering and integrating the analog signals to develop the variable X bias and variable Y bias adjustment signals.

* * * * *